(12) United States Patent
Sweetman et al.

(10) Patent No.: US 8,053,606 B2
(45) Date of Patent: Nov. 8, 2011

(54) ALKOXYLATION OF FLUORINATED ALCOHOLS

(75) Inventors: Karl Jeffrey Sweetman, Wilmington, DE (US); Scott Andrew Backer, Philadelphia, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 238 days.

(21) Appl. No.: 12/432,825

(22) Filed: Apr. 30, 2009

(65) Prior Publication Data

US 2010/0280281 A1    Nov. 4, 2010

(51) Int. Cl.
*C07C 41/01* (2006.01)
*B01J 31/02* (2006.01)
*B01J 31/16* (2006.01)

(52) U.S. Cl. ........ 568/615; 568/677; 502/150; 502/164; 502/169

(58) Field of Classification Search .................. None
See application file for complete search history.

(56) References Cited

U.S. PATENT DOCUMENTS

| | | | |
|---|---|---|---|
| 2,537,981 A | 1/1951 | Edwards | |
| 3,372,201 A | 3/1968 | Leary et al. | |
| 4,533,759 A | 8/1985 | Harris | |
| 4,727,199 A | 2/1988 | King | |
| 4,754,089 A * | 6/1988 | Matson et al. | 570/260 |
| 4,873,017 A | 10/1989 | King | |
| 4,880,894 A | 11/1989 | Sunkel et al. | |
| 4,885,396 A | 12/1989 | Hahn et al. | |
| 5,011,713 A | 4/1991 | Lenti et al. | |
| 5,025,094 A | 6/1991 | King | |
| 5,136,106 A | 8/1992 | King | |
| 5,491,261 A | 2/1996 | Haniff et al. | |
| 5,567,857 A | 10/1996 | Huang et al. | |
| 5,608,116 A * | 3/1997 | Halling et al. | 568/615 |
| 5,633,420 A | 5/1997 | Theriot et al. | |
| 5,948,478 A | 9/1999 | Lenti et al. | |
| 2002/0128521 A1 | 9/2002 | Priou et al. | |
| 2003/0139521 A1 | 7/2003 | Linert et al. | |
| 2007/0032591 A1 | 2/2007 | Durali et al. | |
| 2008/0093582 A1 | 4/2008 | Nagai et al. | |

FOREIGN PATENT DOCUMENTS

| | | |
|---|---|---|
| DE | 102005051939 | 5/2007 |
| DE | 102006010034 | 9/2007 |
| EP | 695772 | 2/1996 |
| JP | 60146848 | 8/1985 |
| JP | 02188545 | 7/1990 |
| JP | 07165832 | 6/1995 |
| JP | 10081873 | 3/1998 |
| JP | 2003292989 | 10/2003 |
| SU | 895492 | 1/1981 |
| WO | WO95/35272 A1 | 12/1995 |

OTHER PUBLICATIONS

Yadav et al., Novelties of kinetics of chemoselective reduction of citronellal to citronellol by sodium borohydride under liquid-liquid phase transfer catalysis, Journal of Molecular Catalysis A: Chemical, vol. 247, Is. 1-2, Mar. 2006, pp. 253-259.*

Chen, Qing-Yun et al.,Studies on Fluoroalkylation and Fluoroalkoxylation. Part 26. Wilkinson's catalyst-induced Addition of Fluoroalkyl Iodides to Olefins, Journal of Fluorine Chemistry, 39, (1988) 217-226, Elsevier Sequoia, the Netherlands.

Abstract of Chen, Qing-Yun et al., Fluoroalkylation and Fluoroalkoxylation. Part 25. Triethylamine/formic acid-induced Free Radical Addition of Fluoroalkyl Iodides to Olefins, Youje Huaxue, (1988), 8, (4), 331-333, Shanghai Institute Organic Chemical, Academy Sin, Shanghai, People's Republic of China.

Abstract of Chen, Qing-Yun et al., Fluoroalkylation and Fluoroalkoxylation. Palladium(0)-catalyzed Addition of Fluoroalkyl Iodide to Olefin, Huaxue Xuebao, (1985), 43(11), 111801120, Shanghai Institute organic Chemical, Academy Sin, Shanghai, People's Republic of China.

Abstract of Gupton, John et al., Phase Transfer Catalyzed Fluoroalkoxylation of Haloaromatic and Haloheteroaromatic Systems, Synthetic Communications, (1985), 15(5), 431-441, Dept. Chemical. University Central Florida, Orlando, FL.

* cited by examiner

*Primary Examiner* — Rosalynd Keys

(74) *Attorney, Agent, or Firm* — Nancy S. Mayer

(57) ABSTRACT

A fluorinated alkylalkoxylate, and a process for its preparation in which at least one fluorinated alcohol is contacted with at least one alkylene epoxide in the presence of a catalyst system comprising an alkali metal borohydride, and an organic quaternary salt.

10 Claims, No Drawings

ALKOXYLATION OF FLUORINATED ALCOHOLS

FIELD OF THE INVENTION

This invention relates to a fluorinated alkylalkoxylate, and a process for its preparation in which a fluorinated alcohol is contacted with an alkylene epoxide in the presence of a catalyst system comprising an alkali metal borohydride, and an organic quaternary salt.

BACKGROUND OF THE INVENTION

Materials containing alcohol alkoxylate have been used in a wide variety of industrial applications, for example as nonionic surfactants. They are typically prepared by the reaction of an alcohol with an alkylene epoxide such as ethylene oxide (i.e., oxirane) or propylene oxide (i.e., 2-methyoxirane) in the presence of one or more catalysts. Fluorinated alkylalkoxylates which are prepared by the reaction of an alcohol incorporating a fluorinated alkyl group with an alkylene epoxide are an important class of materials. Fluorinated alkylalkoxylates are especially useful in several industrial applications, including use as nonionic surfactants in various areas including the manufacture of polyvinylchloride (PVC) films, electrochemical cells, and various photographic and other coatings.

Known catalyst systems and processes for the alkoxylation of fluorinated alcohols include using Lewis acids such as boron trifluoride or silicon tetrafluoride, alone in combination with metal hydrides, fluorides, alkyls or alkoxides. Unfortunately, such acidic materials also catalyze side reactions such as dimerization of alkylene epoxides to form dioxanes during the alkylalkoxylation. The use of strong bases as catalysts alone is not satisfactory for alkoxylation of fluorinated alcohols.

U.S. Pat. No. 5,608,116 discloses a process for the preparation of fluoralkylalkoxylates in which a commercial mixture of perfluoroalkylethanols having the general structure $R_fCH_2CH_2OH$ wherein $R_f$ is a linear or branched perfluoroalkyl group of up to 30 carbon atoms is alkoxylated in the presence of a catalyst system comprising an iodine source and alkali metal borohydride.

The fluorinated materials derived from long chain perfluoroalkyl groups having 8 or more carbons are expensive. Therefore, it is desirable to reduce the fluorine content through use of short chain fluorinated groups and partially fluorinated groups which can deliver the same or even better performance compared to the long chain perfluoroalkyl groups. The catalyst system disclosed in U.S. Pat. No. 5,608,116 is not satisfactory for alkoxylation of alcohols having short chain or partially fluorinated groups. This catalyst system suffers from low reactivity and poor reaction rates when alcohols having short chain or partially fluorinated groups are employed.

A process is needed using a catalyst system which provides desirable reactivity in the alkoxylation of alcohols having short chain or partially fluorinated groups. The present invention provides such a process and the resulting fluorinated alkylalkoxylates.

BRIEF SUMMARY OF THE INVENTION

The present invention comprises a process for the preparation of the compound of Formula (1a):

(1a)

wherein
$R_f$ is a linear or branched perfluoroalkyl group of 1 to 6 carbon atoms;
n is 0 to 4;
X is O;
m is an integer from 1 to 6; and
p is an integer from 1 to about 40;
comprising contacting a fluorinated alcohol of Formula (4)

(4)

wherein
$R_f$ is a linear or branched perfluoroalkyl group of 1 to 6 carbon atoms;
n is 0 to 4;
m is an integer from 1 to 6; and
X is O;
with an alkylene oxide having 2 to 10 carbon atoms, or a mixture of said alkylene oxides, in the presence of a catalyst system comprising (1) at least one alkali metal borohydride, and (2) at least one organic quaternary salt. Optionally a halogen source selected from the group consisting of an alkali metal halide, an alkaline earth metal halide, elemental halogen, and mixtures thereof, is present in the catalyst.

The present invention further comprises a catalyst system comprising (1) an alkali metal borohydride, and (2) at least one organic quaternary salt.

DETAILED DESCRIPTION OF THE INVENTION

All trademarks are denoted herein by capitalization.

The present invention comprises a process for the preparation of a fluorinated alkylalkoxylate of Formula (1)

(1)

wherein
$R_f$ is a linear or branched perfluoroalkyl group of 1 to 6 carbon atoms;
n is an integer from 1 to 4;
X is O;
m is an integer from 1 to 6; and
p is an integer from 1 to about 40.

Preferred compounds of Formula (1) are those wherein $R_f$ is a perfluoroalkyl having 4 or 6 carbons. Also preferred are those compounds of Formula (1) wherein m is 1 to 4, more preferably 2 to 4. Also preferred are those compounds of Formula (1) wherein p is an integer from 1 to about 30, preferably 1 to 20, and more preferably 4 to 13.

The compounds of Formula (1) are prepared by a process in which at least one partially fluorinated alcohol containing a $R_f(CH_2CF_2)_n$— moiety wherein $R_f$ is a short perfluoroalkyl group having 1 to 6 carbon atoms is contacted with an alkylene epoxide in the presence of a catalyst system comprising an alkali metal borohydride and an organic quaternary salt. Details of the process of preparation are described below.

The fluorinated alkylalkoxylates of Formula (1) are especially useful in several industrial applications, including use as nonionic surfactants in the manufacture of polyvinylchloride (PVC) films, electrochemical cells, and various photographic coatings. One of the desired properties of the fluorinated alkylalkoxylates of the present invention is their ability to lower surface tension at very low concentration in aqueous media. Typically use of the compounds of Formula (1) results in surface tensions of less than 25 mN/m at 0.1% in water. This surfactant property results in uses in many aqueous media including various coatings, such as paints, stains, polishes, and other coating compositions, especially as leveling and anti-blocking agents. The compounds of the present invention are also useful in various oil field operations.

$R_f$ is a short perfluoroalkyl group with no more than 6 carbon atoms. One of the advantages of the fluorinated alkylalkoxylates of Formula (1) is that they provide desired surface properties while increasing fluorine efficiency. By the term "fluorine efficiency" as used herein is meant the ability to use a minimum amount of fluorinated compound and lower level of fluorine to obtain the same or enhanced surface properties. The compounds of Formula (1) are also useful as surfactants to reduce surface tension, and have low critical micelle concentration, while having reduced fluorine content due to the partial fluorination and/or short perfluoroalkyl chain length of 6 carbons or less.

A method of altering the surface behavior of a liquid comprises adding to the liquid a compound of a Formula (1) as defined above. Normal surface tension of deionized water is 72 dynes/cm (72 mN/m). The above compound of Formula (1) is a surfactant which lowers surface tension at a specified rate. Generally better performance is obtained at higher concentrations of the surfactant in water. Such surface tension values in a medium, typically a liquid, are less than about 25 milli-newtons per meter (mN/m), preferably less than about 21 milli-newtons per meter (mN/m), at a concentration of the surfactant in the medium of less than about 0.5% by weight.

The method includes altering surface behavior, typically for lowering surface tension and critical micelle concentration (CMC) values, in a variety of applications, such as in coatings, cleaners, oil field agents, and many other applications. Types of surface behavior which can be altered using the method of the present invention include wetting, penetration, spreading, leveling, flowing, emulsifying, dispersing, repelling, releasing, lubricating, etching, bonding, antiblocking, foaming, and stabilizing. Types of liquids which can be used in the method of the present invention include a coating composition, latex, paint, stain, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor finish, or bonding agent.

The compounds of Formula (1) and method are useful in a variety of applications where a low surface tension is desired, such as coating formulations for glass, wood, metal, brick, concrete, cement, natural and synthetic stone, tile, synthetic flooring, paper, textile materials, plastics, and paints. The compounds and method are useful in waxes, finishes, and polishes to improve wetting, leveling, and gloss for floors, furniture, shoe, and automotive care. The compounds and method are also useful in a variety of aqueous and non-aqueous cleaning products for glass, tile, marble, ceramic, linoleum and other plastics, metal, stone, laminates, natural and synthetic rubbers, resins, plastics, fibers, and fabrics. The compounds of Formula (1) are also useful in oil field agents used for drilling and stimulation applications.

The present invention comprises a process for the preparation of the compounds of Formula (1a):

$$R_f-(CH_2CF_2)_n(CH_2)_m-(OCH2CH2)_p-XH \qquad (1a)$$

wherein
$R_f$ is a linear or branched perfluoroalkyl group of 1 to 6 carbon atoms;
n is 0 to 4;
X is O;
m is an integer from 1 to 6; and
p is an integer from 1 to about 40.

The process of the present invention comprises contacting a fluorinated alcohol of Formula (4) or a mixture of such fluorinated alcohols;

$$R_f-(CH_2CF_2)_n(CH_2)_m-XH \qquad (4)$$

wherein
$R_f$ is a linear or branched perfluoroalkyl group of 1 to 6 carbon atoms;
n is 0 to 4;
m is an integer from 1 to 6; and
X is O;
with one or more alkoxylating agents, such as alkylene epoxide, in the presence of a catalyst system comprising (1) an alkali metal borohydride and (2) at least one organic quaternary salt. Optionally an iodine source selected from the group consisting of an alkali metal iodide, an alkaline earth metal iodide, elemental iodine, and mixtures thereof are also present. The catalyst system is effective in the absence of promoters or other catalysts such as strong bases, although such materials can be present if desired.

The compounds of Formula (1) are included within Formula (1a).

Suitable fluorinated alcohols for use as a reactant in the process of the present invention are those of Formula (4) as defined above. Preferred alcohols are those wherein $R_f$ is a perfluoroalkyl group of 4 to 6 carbons, and more preferably 4 carbons. Also preferred are alcohols wherein n is 0 to 3, more preferably 0 to 2, and more preferably 1; m is 1 to 4, preferably 2 to 4, more preferably 2.

Any of a number of alkoxylating agents can be used as a reactant in the process of the present invention. Preferred is an alkylene epoxide. Of these ethylene oxide (oxirane), propylene oxide (2-methyloxirane), and mixtures of these are preferred. The two or more ethylene oxides can be added as a mixture, or added sequentially. Most preferred is the use of ethylene oxide alone due to faster reactivity.

The contacting is conducted in the presence of the catalytic system at a temperature in the range between about 90° C. and 200° C. Preferred for commercial operations is to conduct the process at a temperature of from about 120° C. to about 170° C. Temperature is maintained within a suitable range by appropriate means known in the art. The process is conducted at pressures of from atmospheric pressure to about 100 psig (791×10³ Pa). Preferred is a pressure of from about atmospheric to 50 psig (446×10³ Pa), more preferably from about 20 psig (239×10³ Pa) to about 50 psig (446×10³ Pa).

The process of the present invention permits flexibility in its operation. The catalyst can be added to the fluorinated alcohol prior to or during the addition of the alkoxylating agent. Preferably the fluorinated alcohol is mixed with the catalyst prior to addition of the alkoxylating agent and heating.

The catalytic system used in the process of the present invention is comprised of two elements as follows: (1) an alkali metal borohydride and (2) at least organic quaternary salt. At least one halogen source selected from the group consisting of an alkali metal halide, an alkaline earth metal halide, elemental halogen, and mixtures thereof can optionally be present in the catalyst system.

The alkali metal borohydrides suitable for use in the catalyst system used in the process of the present invention include sodium borohydride, sodium triethyl borohydride, potassium borohydride, and lithium borohydride. Sodium borohydride is preferred. The mole ratio of alkali metal borohydride in the catalyst to fluorinated alcohol can vary widely and is at least from about 0.005 to 1.0, or higher. The upper limit is imposed only by practical considerations such as the cost of excessive borohydride use, contamination of product and waste streams with excess borohydride, and potential difficulty in controlling the rate of the exothermic alkoxylation reaction. Preferably the mole ratio is from about 0.005:1.0 to about 0.25:1.0. The optimum mole ratio of borohydride to fluorinated alcohol will be affected by such factors as the structures of the fluorinated alcohol and alkoxylating agent, and the temperature, pressure and cooling efficiency of the reaction vessel. For the reaction of an alkylene oxide, such as ethylene oxide, propylene oxide, butylene oxide, styrene oxide and the like, with fluorinated alcohols useful for the purposes of this invention at 100° C. to 145° C. under atmospheric pressure, the preferred mole ratio borohydride to fluorinated alcohol is in the range between about 0.025 to 1.0 and more preferably from about 0.1 to 1.0.

The organic quaternary salt suitable for use in the catalyst system used in the process of the present invention includes one or more groups of Formula (2)

   (2)

wherein

Q is an element of Group Vb of the Periodic Table selected from the group consisting of nitrogen, phosphorus, arsenic, antimony, and bismuth;

each $R^1$ is independently selected from the group consisting of a $C_1$ to $C_{16}$ alkyl, a $C_1$ to $C_{16}$ aryl, a $C_1$ to $C_{16}$ alkaryl, a $C_1$ to $C_{16}$ aralkyl, a $C_1$ to $C_{16}$ cycloalkyl, a $C_1$ to $C_{16}$ fluoroalkyl radical, and a $C_1$ to $C_{16}$ aromatic carbocyclic optionally containing fluorine and optionally substituted with alkyl, provided that the total number of carbon atoms in the four $R^1$ moieties is at least 16;

Y is a halogen or carboethoxy radical.

The preferred organic quaternary salts suitable for use in the catalyst system used in the process of the present invention are of Formula (2) wherein $R^1$ is selected from the group consisting of alkyl, aryl, alkaryl, aralkyl, and cycloalkyl radicals, provided that the total number of carbon atoms in the four $R^1$ moieties is at least 16, and is preferably from about 28 to 40. Also preferred are quaternary salts wherein Q is nitrogen and phosphorus.

Examples of specific organic quaternary salts of Formula (2) suitable for use in the catalyst system used in the present invention include the following:

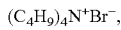

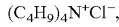

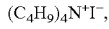

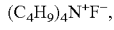

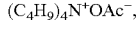

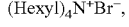

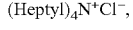

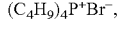

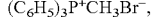

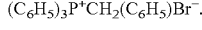

Many other specific organic quaternary salts represented by Formula (2), $[(R^1)_4Q]^+Y^-$, as described above are also suitable for use in the catalyst system used in the present invention. Examples of commercially available salts useful as catalysts herein include methyltricapryl ammonium chloride, and methyltrialkyl ($C_8$-$C_{10}$) ammonium chloride, both available from Aldrich Chemical Company, Milwaukee, Wis.

No theoretical maximum number of carbon atoms for inclusion in the quaternary salts exists, although in general, where the phases involved in the reaction system are aqueous and organic, about 70 carbon atoms represents the upper limit imposed by certain practical limitations. One of the hydrocarbons in Formula (2) can be further substituted by a quaternary group to form a di-quaternary salt represented by Formula (3)

wherein Q, Y and $R^1$ are as defined in Formula (2).

Di-quaternary salts of Formula (3) are also suitable for use in the catalyst system used in the present invention. Further, multifunctional quaternary salts in which the general formula $[(R^1)_4Q]^+Y^-$ (2) is repeated and bonded together a plurality of times can also be used in the process of the present invention effectively. Mixtures of such salts including mono-, di-, and multifunctional quaternary salts can also be used in the process of the present invention.

The amount of the quaternary salt which is employed in the catalyst is subject to considerable variation. The quaternary salts described herein suitable for the purpose of alkoxylating fluorinated alcohols in the presence of an alkali metal borohydride are employed in mole ratios of Q in Formulas 2 and 3 to alkali metal borohydride of from about 0.1:1 to about 3:1.

Halogen sources suitable for use in the catalyst system used in the process of the present invention include elemental halogen, lithium halide, sodium halide, potassium halide, calcium halide, and halides of the elements of Group Vb of the Periodic Table. Within the halogen sources preferred halogens are iodine, bromine, and chlorine. The preferred halogen source is elemental halogen, sodium halide, or a mixture of the same. Especially preferred for use in the catalyst system of the present invention is iodine, sodium iodide, or a mixture thereof. The mole ratio of halogen source to alkali metal borohydride is in the range between about 0.01:10 and about 300:1. For the reaction of an alkylene oxide with fluorinated alcohols useful for the purposes of this invention at 100° C. to 145° C. under atmospheric pressure, the preferred mole ratio of halogen source to alkali metal borohydride is in the range between about 0.1:1.0 and about 0.5:1.0, and the most preferred mole ratio is in the range between about 0.1:1.0 and 0.3:1.0. At high levels of halogen source relative to borohydride, the alkoxylation reaction tends to be inhibited and the rate of reaction may slow.

As previously noted the catalyst system used in the process of the present invention comprises a mixture of 1) an alkali metal borohydride, and 2) an organic quaternary salt. While not wishing to be bound by theory, it is believed that the catalytic activity of the quaternary salts is considered as phase transfer catalysis. This is characterized by marked solubility of the salt in the less polar of the distinct phases. A substantial increase in the extent or the rate at which the reactants and products in the several phases react with each other occurs due to the presence of the catalyst system.

Certain organic quaternary salts, usually ammonium or phosphonium quaternary salts are affected by introduction to the reaction process as phase transfer catalysts which are more soluble in the least polar reactant-containing phase than in the other reactant-containing phases. More specifically, use of these organic quaternary salts as phase transfer catalysts can be affected in a heterogeneous reaction system. Herein the term of "heterogeneous reaction" means that reactants and/or products involved in the reaction are located in distinct phases, including liquid-liquid or liquid-solid phases. These organic quaternary salts can effectively catalyze such heterogeneous reactions by transferring reactants, products, ions or other reactive or functional groups, across the phase interface between the distinct phases. For example, the distinct phases which contain the reactants or products will differ in polarity and/or solubility and the organic quaternary salts will be selected to be preferentially soluble in the less polar phases. The organic quaternary salt also can shift reactants, products, ions or other reactive or functional groups across two, or multiple distinct phases to facilitate the heterogeneous reaction.

Solvents suitable for use in the process of the present invention are those which exhibit distinct solubility of the reactants and products used in the process of the present invention. Some can also be considered to enhance reactivity. Examples of such solvents include ethylene glycol dimethyl ether (also called dimethyl ethylene glycol, or glyme), di-ethylene glycol dimethyl ether (also called dimethyl diethylene glycol, or diglyme), tri-ethylene glycol dimethyl ether (also called trimethyl diethylene glycol, or triglyme), or tetra-ethylene glycol dimethyl ether (also called tetramethyl diethylene glycol, or tetraglyme), and cyclic ethers, such as ethylene oxide cyclic hexamer (CAS RN: 17455-13-9) and ethylene oxide cyclic pentamer (CAS RN: 33100-27-5), and the like, and mixtures thereof. The selection of these solvents suitable for the process of the present invention depends on their solubility in distinct phases, their boiling points, and the ability to remove them.

Inert materials or other solvents can be also present during the reaction. In a preferred embodiment the fluorinated alcohol or alcohol mixture is contacted in neat form with the alkoxylating agent in the presence of the catalytic system. It is also preferable that the fluorinated alcohol be thoroughly dried using methods known to those skilled in the art prior to reaction with the alkoxylating agent to avoid undesirable side reactions. The process of the present invention can be successfully applied to the alkoxylation of non-fluorinated alcohols as well.

In one specific embodiment of the process of the present invention, the fluorinated alkylalkoxylates of Formula (1) defined above are prepared by the reaction of a fluorinated alcohol having the general structure of Formula (4), $R_f(CH_2CF_2)_n(CH_2)_mXH$, as defined above, with ethylene oxide in the presence of the above described catalyst in accordance with the following equation:

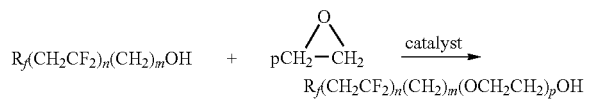

The fluorinated alcohols of Formula (4) used as reactants in the process of the present invention

$$R_f(CH_2CF_2)_n(CH_2)_m\text{—OH} \quad (4)$$

wherein $R_f$ is a linear or branched perfluoroalkyl group having 1 to 6 carbon atoms, subscript n is 0 to 4, and m is an integer from 1 to 6, preferably 1 to 4, more preferably 2 to 4, are available by synthesis according to the following Scheme 1 when n is a positive integer:

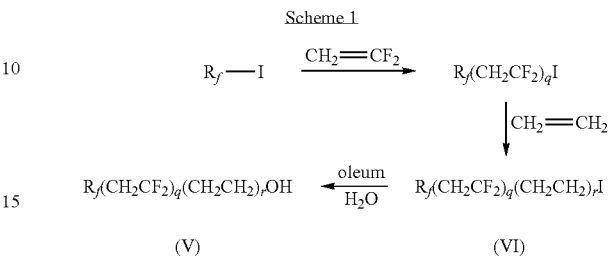

The reaction of vinylidene fluoride with linear or branched perfluoroalkyl iodides produces compounds of the structure $R_f(CH_2CF_2)_qI$, where $R_f$ is as defined as in Formula (5) and q is 1 to 4. For example, see Balague, et al, "Synthesis of fluorinated telomers, Part 1, Telomerization of vinylidene fluoride with perfluoroalkyl iodides", J. Fluorine Chem. (1995), 70(2), 215-23. The specific telomer iodides are isolated by fractional distillation. The telomer iodides are treated with ethylene by procedures described in U.S. Pat. No. 3,979,469 to provide the telomer ethylene iodides (VI of Scheme 1) wherein r is 1 to 3 or more, and q is 1 to 4. The telomer ethylene iodides (VI of Scheme 1) are treated with oleum and hydrolyzed to provide the corresponding telomer alcohols (V of Scheme 1) according to procedures disclosed in WO 95/11877. Alternatively, the telomer ethylene iodides (VI of Scheme 1) can be treated with N-methyl formamide followed by ethyl alcohol/acid hydrolysis.

Fluorinated alcohols of formula (4) wherein n is 0 are known and commercially available. They are prepared by conventional methods such as by the klomerization of tetrafluoromethylene in the presence of suitable catalysts followed by ethylation and hydrolyses. See, U.S. Pat. No. 5,097,090.

The following equipment and test method were used in the Examples herein.

Equipment

A 250 ml round bottom flask (RBF) was used as reactor. The flask was equipped with a gas inlet tube connected to an ethylene oxide (EO) feed line, a dry ice condenser, and a mechanical agitator. A thermocouple connected to a J-KEM, Gemini controller (from J-KEM Scientific, Inc., St. Louis, Mo.) was used to control batch temperature.

The ethylene oxide (EO) feed line included a 2.27 kg ethylene oxide cylinder, mounted on a lab balance. The ethylene oxide cylinder was equipped with an exterior shut-off gate valve and connected in series with a check valve and a needle control valve. This EO feed was via a T-line connected to a dry nitrogen flow to allow a mixture of nitrogen and EO to enter the reactor. A dry trap was inserted just before the reactor to buffer the EO feed line against unanticipated reactor back flow. Flow was monitored by a gas bubbler filled with KRYTOX, available from E. I. du Pont de Nemours and Company, Wilmington, Del., and two rotameters in line with both the nitrogen and the EO individually.

A scrubber system included an exit line from the dry ice condenser. The exit line passed through a KRYTOX exit bubbler and then through two scrubber bottles; one dry bottle to act as a buffer between the reactor and the scrubber and, the second scrubber was filled with 10% aqueous sodium hydroxide.

Test Method 1—Surface Tension Measurement

Surface tension was measured using a Kiruess Tensiometer, K11 Version 2. 501 in accordance with instructions with the equipment. The Wilhelmy Plate method was used. A vertical plate of known perimeter was attached to a balance, and the force due to wetting was measured. Samples to be tested were diluted with water. Each Example was added to deionized water by weight based on solids of the additive in deionized water; Standard Deviation was less than 1 dynes/cm (1 mN/m); Temperature was about 21° C. Normal surface tension of deionized water is 72-73 dynes/cm (72-73 mN/m). Ten replicates were tested of each dilution, and the following machine settings were used: Method: Plate Method SFT; Interval: 1.0 s; Wetted length: 40.2 mm; Reading limit: 10; Min Standard Deviation: 2 dynes/cm (2 mN/m); Gr. Acc.: 9.80665 m/s$^2$.

EXAMPLES

Example 1

A clean dry round bottom flask (RBF) was charged with 40 grams of distilled $C_4F_9(CH_2CF_2)_nCH_2CH_2OH$ (121.9 mmols), wherein predominantly n=1; 0.175 grams (1.16 mmols) of sodium iodide, 0.20 grams (5.29 mmols) of sodium borohydride and 0.43 grams (1.17 mmols) of tetra-n-butylammonium iodide. The reactor was heated under $N_2$ purge (no EO feed) to about 125° C. and held for 1 hour to complete the evolution of hydrogen during catalyst formation. After the evolution of hydrogen had ceased, as indicated by the absence of bubbling in the exit bubbler with the nitrogen purge turned off, the EO feed was started. Ethylene oxide was introduced in small 1-4 gram increments while maintaining at about 125° C.±15° C. Addition of ethylene oxide was continued over 6 days in shifts of about 3-8 hours, allowing the reaction mixture to cool and stand under nitrogen during overnight period The reaction was run at atmospheric pressure. The addition of ethylene oxide to the reactor was estimated by difference in the gross weight of the ethylene oxide cylinder between additions. The addition of ethylene oxide was done at atmospheric pressure and unreacted ethylene oxide evaporated to the scrubber. The progress of the reaction was characterized by $^1$H NMR ($CD_2Cl_2$/trifluoroacetic anhydride, 500 MHz) and is shown in Table 1 as the (EO#) or ethylene oxide number of the ethoxylated alcohols, also known as the degree of polymerization (DP). (EO#) for the purpose of this experiment is defined as: Moles of ethylene oxide (EO) divided by moles of ethoxylated alcohols. At the end of day 1 of the reaction, about 6.5 grams of EO (accumulative amount) was admitted to the flask, and the (EO #) was 1.4. At the end of day 2, about 25-27 grams of EO (accumulative amount) was admitted to the flask, and the EO # was 1.5. After day 3, it was apparent that EO uptake was too sluggish and an additional 0.18 grams of NaI, 0.18 grams of NaBH$_4$, and 0. 43 grams of tetra-n-butyl ammonium iodide were added to the reaction mixture. The mixture was reheated to 80° C. and held for 1 hour to allow for catalyst formation and to vent the evolved hydrogen. Hydrogen evolution was followed as described above. Ethylene oxide addition was restarted and the mixture was sampled and characterized by $^1$H NMR ($CD_2Cl_2$/trifluoroacetic anhydride, 500 MHz) with time as follows. At the end of day 4, about 45-47 grams of EO (accumulative amount) was admitted to the flask and EO # was 3.4. At the end of day 5, about 50-52 grams of EO (accumulative amount) was admitted to the flask, and the EO # was 5.9. At the end of day 6, about 53-55 grams of EO (accumulative amount) was admitted to the flask, and EO # was 6.4. After the addition of ethylene oxide on day 6, the mixture was cooled to room temperature and the reaction mass totaled 65.2 grams. The final product from day 6 was characterized by $^1$H NMR ($CD_2Cl_2$/trifluoroacetic anhydride, 500 MHz) as $C_4F_9(CH_2CF_2)_nCH_2CH_2(OCH_2CH_2)_p$—OH, predominantly n=1 and p was about 6.4. The progress of the reaction and the conversion is shown in Table 1. The final product of the end of day 6 from Example 1 was added to water and tested for surface tension according to the Test Method 1. Results are in Table 4.

TABLE 1

| Ethylene oxide Admitted to the Reactor (gms) | EO # Of the ethoxylate (degree of Polymerization) | Mole % of reaction mixture | |
|---|---|---|---|
| | | Free alcohol | Ethoxylated alcohols |
| 6 | 1.4 | 64 | 36 |
| 25-27 | 1.5 | 52 | 48 |
| 45-47 | 3.4 | 10 | 90 |
| 50-52 | 5.9 | 3.1 | 96.9 |
| 53-55 | 6.4 | 1.1 | 98.9 |

In Table 1, EO=ethylene oxide; EO#=moles of ethylene oxide/moles of ethoxylated alcohols.

The data in Table 1 shows that a high percentage of alcohol was converted to ethoxylated alcohol using the process of the present invention.

Comparative Example A

A clean dry round bottom flask was charged with 40 grams of distilled $C_4F_9(CH_2CF_2)_nCH_2CH_2OH$ (121.9 mmols), predominantly n=1; 0.35 gms (2.33 mmols) of sodium iodide, and 0.20 grams (5.29 mmols) of sodium borohydride. The reactor was heated under nitrogen purge (no ethylene oxide feed) to about 125° C. and held for about 1 hour to complete the evolution of hydrogen. Then 40 gms of ethylene oxide were added to the flask incrementally in the same process as Example 1. After the reaction a portion of the reaction mixture was distilled under vacuum at, 126° C., 12 mm Hg (1600 Pa), to remove excess $C_4F_9(CH_2CF_2)_nCH_2CH_2OH$. The free alcohol distillate fraction weighed 17.5 gms and the ethoxylated pot residue weighed 11.5 gms. The final product ethoxylate residue was characterized by $^1$H NMR ($CD_2Cl_2$ trifluoroacetic anhydride, 500 MHz) as $C_4F_9(CH_2CF_2)_nCH_2CH_2(OCH_2CH_2)_p$—OH, predominately n=1 and p was about 1.9. The progress of the reaction and the conversion is shown in Table 2.

TABLE 2

| Ethylene oxide Admitted to the Reactor (gms) | EO # Of the ethoxylate (degree of Polymerization) | Mole % of reaction mixture | |
|---|---|---|---|
| | | Free alcohol | Ethoxylated Alcohols |
| 40 | 1.9 | 65 | 35 |

In Table 2, EO=ethylene oxide; EO#=moles of ethylene oxide/moles of ethoxylated alcohols.

The data in Table 2 shows only 35% conversion to ethoxylated alcohols. A comparison to Example 1 (Table 1) shows that the process of the present invention converted a higher percent after use of 25-27 moles of ethylene oxide, and 90% conversion after use of 45-47 moles of ethylene oxide, thus demonstrating the superiority of the process of the present invention.

Example 2

A clean dry (round bottom flask) RBF was charged with 40 grams of distilled $C_4F_9(CH_2CF_2)_nCH_2CH_2OH$ (121.9 mmols), predominantly n=1; 0.20 gms (1.33 mmols) of sodium iodide), 0.20 grams (5.29 mmols) of sodium borohydride and 0.47 grams (1.16 mmols) of methyl triphenylphosphonium iodide. The reactor was heated under nitrogen purge (no EO feed) to about 80° C. and held for about 1 hour to complete the evolution of hydrogen during catalyst formation. After the evolution of hydrogen had ceased, as indicated by the absence of bubbling in the exit bubbler with the nitrogen purge turned off, the EO feed was started. Ethylene oxide was introduced in small 1-4 gram increments while attempting to maintain 125° C.±15° C. Addition of ethylene oxide was continued over 6 days in shifts of about 3-8 hours, allowing the reaction mixture to cool and stand under nitrogen during overnight periods. Because the reaction was run at atmospheric pressure the addition of ethylene oxide to the reactor was estimated by difference in the gross weight of the ethylene oxide cylinder between additions. Any unreacted ethylene oxide was evaporated to the scrubber. The progress of the reaction was characterized by $^1H$ NMR ($CD_2Cl_2$/trifluoroacetic anhydride, 500 MHz) by the method described in Example 1. At the end of day 2, about 6.0 grams of EO (accumulative amount) were admitted to the flask, and EO # was 2. After day 2, it was apparent that EO uptake was too sluggish and an additional 0.18 grams of NaI 0.20 grams of $NaBH_4$ were added to the reaction mixture. The mixture was reheated to 125° C. and held for about 1.3 hours to allow for catalyst formation and to vent the evolved $H_2$. Hydrogen evolution was followed as described above. Ethylene oxide addition was restarted and the mixture was sampled with time. At the end of day 3, about 10-12 grams (accumulative amount) of EO were admitted to the flask, and EO # was 1.7. At the end of day 5, about 21-23 grams (accumulative amount) of EO were admitted to the flask, and EO # was 2.3. The reaction still appeared sluggish so an additional 0 47 grams of methyl triphenylphosphonium iodide was added to the flask. At the end of day 6, 47.5-50.5 grams of EO (accumulative amount) admitted to the flask, and EO# was 6.2. After the addition of ethylene oxide on day 6 the mixture was cooled to room temperature and the reaction mass totaled 67.2 grams. The final product from day 6 above was characterized by $^1H$ NMR ($CD_2Cl_2$/trifluoroacetic anhydride, 500 MHz) as $C_4F_9(CH_2CF_2)_nCH_2CH_2(OCH_2CH_2)_p$—OH, predominantly n=1 and p was about 6.2. The progress of the reaction and the conversion is shown in Table 3. The final product from Example 2 was added to water and tested for surface tension according to Test Method 1. Results are in Table 4.

TABLE 3

| Ethylene oxide | EO # Of the ethoxylate | Mole % of reaction mixture | |
|---|---|---|---|
| Admitted to the Reactor (gms) | (degree of Polymerization) | Free alcohol | Ethoxylated alcohols |
| 6.5 | .2 | 82 | 18 |
| 10-12 | 2.2 | 22.6 | 77.4 |
| 21-23 | 2.3 | 18.8 | 91.2 |
| 47.5-50.5 | 6.2 | 2.6 | 97.4 |

In Table 3, EO=ethylene oxide; EO#=moles of ethylene oxide/moles of ethoxylated alcohols.

The data in Table 3 shows that a high percentage of alcohol was converted to ethoxylated alcohol using the process of the present invention.

Comparative Example B

A commercial fluoroalkylalkoxylate represented by a formula of $C_xF_{2x+1}CH_2CH_2(OCH_2CH_2)_pOH$ wherein x had a distribution of from about 4 to about 14 and p (average degree of ethoxylation) was about 7, available from E. I. du Pont de Nemours and Company, Wilmington Del., was added to water and tested for surface tension according to the Test Method 1. Results are in Table 4.

TABLE 4

| | Surface Tension Measurement, mN/m | | | | |
|---|---|---|---|---|---|
| Example | Deionized water | 0.001% | 0.010% | 0.100% | 0.500% |
| Example 1 | 72.3 | 52.0 | 38.7 | 21.8 | 20.9 |
| Example 2 | 73.8 | 54.2 | 40.2 | 21.9 | 20.5 |
| Comparative Example B | 72.9 | 43.5 | 22.8 | 19.8 | 19.7 |

The data in Table 4 shows that when a compound of the present invention was added, the surface tension of each aqueous solution was reduced significantly. Examples 1 and 2, having six carbons in the perfluoroalkyl group showed comparable surface tension reduction to the Comparative Example B, having a mixture of perfluoroalkyls of 4 to 14 carbons and thus having a higher content of fluorine present.

Comparative Example C

A reactor was charged was charged with 40 grams of distilled $C_4F_9(CH_2CF_2)_nCH_2CH_2OH$ (121.9 mmols), predominantly n=1; 0.35 grams (2.32 mmols) of sodium iodide, and 0.20 grams (5.29 mmols) of sodium borohydride. The reactor was heated under nitrogen purge (no ethylene oxide feed) to about 80° C. and held for about 1 hour to complete the evolution of hydrogen during catalyst formation. The reactor was pressurized with 9 psig ($163 \times 10^3$ Pa) of nitrogen at 0° C. after 20 grams of ethylene oxide was introduced. The reaction was carried out for 12 hours, and the temperature of the reactor was maintained at about 135° C. The pressure of the reactor was about 35-40 psig ($343 \times 10^3$ to $377 \times 10^3$ Pa) at the beginning and dropped as ethylene oxide was consumed, to 9 psig ($163 \times 10^3$ Pa) after complete ethylene oxide consumption each time. The product characterized by $^1H$ NMR ($CD_2Cl_2$/trifluoroacetic anhydride, 500 MHz) as $C_4F_9(CH_2CF_2)_nCH_2CH_2(OCH_2CH_2)_p$—OH, predominantly n=1 and p was about 1.4.

What is claimed is:

1. A process for the preparation of the compound of Formula (1a)

$$R_f\text{—}(CH_2CF_2)_n(CH_2)_m\text{—}(OCH2CH2)_p\text{—}XH \quad (1a)$$

wherein
$R_f$ is a linear or branched perfluoroalkyl group of 1 to 6 carbon atoms;
n is 0 to 4;
X is O;
m is an integer from 1 to 6; and
p is an integer from 1 to about 40;
comprising contacting a fluorinated alcohol of Formula (4)

$$R_f\text{—}(CH_2CF_2)_n(CH_2)_m\text{—}XH \quad (4)$$

wherein
$R_f$ is a linear or branched perfluoroalkyl group of 1 to 6 carbon atoms;
n is an integer from 0 to 4;
m is an integer from 1 to 6;
X is O;
with an alkylene oxide having 2 to 10 carbon atoms, or a mixture of said alkylene oxides, in the presence of a catalyst system comprising (1) at least one alkali metal borohydride and (2) at least one organic quaternary salt.

2. The process of claim 1 wherein the organic quaternary salt is of Formula (2)

$$[(R^1)_4Q]^+Y^- \quad (2)$$

wherein
Q is selected from the group consisting of nitrogen, phosphorus, arsenic, antimony, and bismuth;
each $R^1$ is independently selected from the group consisting of a $C_1$ to $C_{16}$ alkyl, a $C_1$ to $C_{16}$ aryl, a $C_1$ to $C_{16}$ alkaryl, a $C_1$ to $C_{16}$ aralkyl, a $C_1$ to $C_{16}$ cycloalkyl, a $C_1$ to $C_{16}$ fluoroalkyl radical, and a $C_1$ to $C_{16}$ aromatic carbocyclic optionally containing fluorine and optionally substituted with alkyl, provided that the total number of carbon atoms in the four $R^1$ moieties is at least 16; and
Y is a halogen or carboethoxy radical.

3. The process of claim 2 wherein Q is nitrogen or phosphorus.

4. The process of claim 2 wherein the organic quaternary salt is selected from the group consisting of:

$(C_4H_9)_4N^+Br^-$, $(C_4H_9)_4N^+Cl^-$, $(C_4H_9)_4N^+I^-$, $(C_4H_9)_4N^+F^-$, $(C_4H_9)_4N^+OAc^-$, $(Hexyl)_4N^+Br^-$, $(Heptyl)_4N^+Cl^-$, $(C_2H_5)_3N^+CH_2(C_6H_5)Br^-$, $[CH_3(CH_2)15]N^+(CH_3)3Br^-$, $(C_4H_9)_4P^+Br^-$, $(C_6H_5)_3P^+CH_3Br^-$, $(C_6H_5)_3P^+CH_2(C_6H_5)Br^-$.

5. The process of claim 1 wherein the mole ratio of alkali metal borohydride in the catalyst to fluorinated alcohol is from about 0.005:1 to about 0.25:1.

6. The process of claim 1 wherein the mole ratio in the catalyst of moiety Q in the quaternary salt to alkali metal borohydride is from about 0.1:1 to about 3:1.

7. The process of claim 1 wherein the catalyst system further comprises at least one halogen source selected from the group consisting of an alkali metal halide, an alkaline earth metal halide, elemental halogen, and mixtures thereof.

8. The process of claim 7 wherein the mole ratio of halogen source to alkali metal borohydride is from about 0.01:1 to about 300:1.

9. The process of claim 1 conducted in a solvent selected from the group consisting of ethylene glycol dimethyl ether, di-ethylene glycol dimethyl ether, tri-ethylene glycol dimethyl ether, tetra-ethylene glycol dimethyl ether, ethylene oxide cyclic hexamer, ethylene oxide cyclic pentamer and mixtures thereof.

10. The process of claim 1 wherein the contacting is at a temperature from about 100° C. to about 145° C., and at a pressure of from atmospheric pressure to about 100 psig ($791\times10^3$ Pa).

* * * * *